(12) United States Patent
Saint-Jalmes et al.

(10) Patent No.: US 6,486,351 B1
(45) Date of Patent: Nov. 26, 2002

(54) METHOD FOR CONDENSATION OF AROMATIC DERIVATIVE(S) AND A SULPHINIC DERIVATIVE

(75) Inventors: Laurent Saint-Jalmes, Meyzieu (FR); Marc Tordeux, Sceaux (FR); Claude Wakselman, Paris (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/786,665
(22) PCT Filed: Sep. 8, 1999
(86) PCT No.: PCT/FR99/02134
§ 371 (c)(1),
(2), (4) Date: Mar. 7, 2001
(87) PCT Pub. No.: WO00/15585
PCT Pub. Date: Mar. 23, 2000

(30) Foreign Application Priority Data

Sep. 14, 1998 (FR) .............................................. 98/11431

(51) Int. Cl.$^7$ ...................... C07C 233/05; C07C 315/00
(52) U.S. Cl. .......................... 564/218; 564/440; 568/27; 568/36
(58) Field of Search ................................ 564/218, 440; 568/27, 36

(56) References Cited

U.S. PATENT DOCUMENTS 5,618,945 A * 4/1997 Casado et al. ........... 548/367.4

OTHER PUBLICATIONS

L.M. Yagupol'Skii, et al., Journal of Organic Chemistry of the USSR, vol. 20, No. 1, pt. 2, Jan. 1984, pp. 103–106, XP002105248.
V.N. Movchun, et al., Journal of Fluorine Chemistry, vol. 70, No. 2, Feb. 1, 1995, pp. 255–257, XP004020766.

* cited by examiner

Primary Examiner—Shailendra Kumar

(57) ABSTRACT

The invention concerns a method for the condensation of aromatic derivative(s) or a sulphinic derivative by a perhalogenated, advantageously perfluorinated, carbon atom. Said method is characterized in that it consists in subjecting said sulphinic derivative and said aromatic derivative to the action of a strong acid whereof the pKa is not more that 0. The invention is applicable to organic synthesis.

11 Claims, No Drawings

METHOD FOR CONDENSATION OF AROMATIC DERIVATIVE(S) AND A SULPHINIC DERIVATIVE

This application is an application under 35 U.S.C. Section 371 of International Application Number PCT/FR99/02134 filed on Sep. 08, 1999.

A subject matter of the present invention is a process for the condensation of aromatic derivatives and of a sulfinic derivative, the carbonaceous chain of which is attached to the sulfinic functional group via a perhalogenated carbon atom. It relates more particularly to a process for the synthesis of reactants of the type of those developed, firstly, by Professor Yagupol'skii and his team and then by Professor Umemoto and his team.

This perfluoroalkylating reagent exhibits, as alkylating functional group, a sulfonium substituted by two aryls, or an aryl and an alkyl unit, and a perfluoroalkyl.

Access to this type of functional group is particularly difficult. This type of functional group is currently obtained by the action of an aryl perfluoroakyl sulfoxide, which is condensed with an aromatic derivative in the presence of strong acid.

It is the above sulfoxides which present the most difficulties in being synthesized.

The syntheses described by Pr. Yagupol'skii and his team (see in particular Zh. Org. Khim., vol. 20, No. 1, p. 115 to 118, January 1984) and Pr. Umemoto and his team (see in particular Chem. Rev., 1996, 96, p. 1757 to 1777) are both lengthy and difficult.

This is not very surprising, due to the many side reactions which take place in these extremely acidic and relatively unstable media.

This is why one of the aims of the present invention is to provide a process which make possible the synthesis of sulfoxide connected, on the one hand, to a perfluoroalkyl group or more generally to a group exhibiting a perhalogenated carbon atom connected to the sulfoxide functional group and, on the other hand, to an aryl radical.

Another aim of the present invention is to provide a process which makes it possible to obtain perfluoroalkyl diaryl sulfonium.

Another aim of the present invention is to provide a process of the preceding type which makes it possible to link together, in the same reactor, the preparation of the sulfoxide and then of the perfluoroalkyl diaryl sulfonium.

These aims and others which will become apparent subsequently are achieved by means of a process for the condensation of aromatic derivatives and of a sulfinic derivative, the carbonaceous chain of which is attached to the sulfinic functional group via a perhalogenated carbon atom, advantageously a perfluorinated carbon atom, in which process said sulfinic derivative and said aromatic derivative are subjected to the action of a strong acid, the pKa of which is at most equal to zero.

At the present time, this type of reaction can hardly be explained but by the existence in the reaction medium of a protonated form of the sulfinic functional group, a form whose presence is highly improbable and very surprising because of the extreme acidity of perhalosulfinic acids.

Said sulfinic functional group can be chosen in particular from acid, salt or ester functional groups. It is also possible to envisage mixed anhydride functional groups, including acid halides. However, these compounds exhibit the disadvantage of not being very stable and require significant operating precautions.

The forms which directly generate the acid (that is to say, the acid itself and the salts) are preferred.

The acids capable of giving the reaction are chosen in particular from hydrohalic acids, advantageously including sulfonic acids, preferably perhalosulfonic acids, and fluorosulfinic acids, sulfuric acid and their mixtures.

During the study which led to the present invention, it was shown that the presence of water played a significant role in the implementation of the reaction.

Excess water has a tendency to block any reaction; on the other hand, the complete absence of water is capable of promoting undesired side reactions, in particular polymerizations.

Thus, according to the present invention, it is preferable to keep the amount of water involved during the reaction within a restricted range.

It has thus been shown that it is preferable for the $H_2O$/sulfinic functional group molar ratio to be at most equal to 4, advantageously to 3, preferably to 2.

At the other boundary of the range, it is preferable for the $H_2O$/sulfinic functional group ratio to be at least equal to 0.1, advantageously to 0.2 and preferably to 0.5.

The optimum region is thus within approximately 2 and approximately 0.2 for the $H_2O$/sulfinic functional group molar ratio.

Another constraint can be significant as regards the amount of water in the medium.

Thus, if the $H_2O$/strong acid functional group molar ratio is examined, it is preferably at most equal to 2 or better still at most equal to 1 but it has been shown that it is desirable for it to be at least equal to 0.05, advantageously to 0.1, preferably to 1/4.

To solve these problems, it may sometimes be useful to carry out the reactions in the presence of a dehydrating agent.

It is possible to use phosphorus pentoxide ($P_2O_5$) as dehydrating agent. It is also possible to envisage using oleum. However, one of the best dehydrating agents is composed of the symmetrical or mixed anhydrides of perfluoroalkanesulfonic acids. These acids, the commonest of which is the paradigm, is trifluoromethanesulfonic acid, alias triflic acid.

According to the present invention, the reaction can be carried out without a solvent, that is to say that one or more of the components of the reaction mixture, in excess or not in excess, constitutes the solvent.

However, it is possible to envisage solvents for this type of reaction, namely solvents of low basicity. This is because basic solvents, on the one hand, are unstable in the presence of strong acids, such as triflic acid, and, on the other hand, reduce the acidity thereof.

Thus, according to the present invention, it is preferable to use solvents exhibiting a low donor number.

Mention may be made, as examples of organic solvents which can give good results, of halogenated solvents, aliphatic solvents and aromatic solvents which are highly depleted in electron, and their mixture.

One of the advantages of the present invention is that it can be carried out in a fairly wide temperature range. Thus, the invention is advantageously carried out at a temperature at most equal to 100° C., preferably to 80° C., more preferably to 50° C.

It is also desirable for the temperature to be at least equal to the starting melting point, preferably finishing melting point, generally at least equal to 0° C.

The reaction is generally carried out at atmospheric pressure but it can easily be carried out under a higher or lower pressure than atmospheric pressure. The choice of the pressure depends on the reaction medium and on its boiling point.

When an ester is used as sulfinic functional group, it is preferable for the alcohol to be a primary alcohol, advantageously a $C_1$–$C_4$ alcohol.

As regards them, it should be pointed out that the richest substrates, such as anisol, give mediocre results; this is perhaps due to side reactions related to the rich doublet of the oxygen.

On the other hand, very good results are obtained with relatively slightly enriched nuclei, such as alkylbenzenes, or relatively slightly depleted nuclei, such as benzene nuclei substituted by halogens; highly depleted aromatic nuclei are needed for a significant fall in the reactivity, as in the case of trifluoromethylbenzenes.

Said carbonaceous chain is advantageously a radical described as a perfluoroalkyl (Rf) radical; this term is preferably understood to mean radicals of formula:

—$(CX_2)_p$—EWG where
the X groups, which are alike or different, represent a halogen (advantageously represents at least one fluorine, preferably at least 2, per carbon) or a radical of formula $C_nF_{2n+1}$ with n an integer at most equal to 5, preferably to 2;
where p represents an integer at most equal to 2;
where EWG represents an electron-withdrawing group, the possible functional groups of which are inert under the reaction conditions, advantageously fluorine or a perfluorinated residue of formula $C_nF_{2n+1}$ with n an integer at most equal to 8, advantageously to 5.

The total carbon number of Rf is advantageously between 1 and 15, preferably between 1 and 10.

Some of the compounds synthesized in the examples are novel compounds.

The following nonlimiting examples illustrate the invention.

1) Procedure in Triflic Acid

Synthesis of 2,4-dichlorophenyl trifluoromethyl sulfoxide

Sodium triflinate (2.37 g, 15 mmol), then 6 equivalents of triflic acid (21.65 g, 144 mmol), after stirring for a few minutes, more than one equivalent of 1,3-dichlorobenzene (3.22 g, 22 mmol) and finally one equivalent of triflic anhydride (4.32 g, 15 mmol) are introduced into a three-necked flask surmounted by a reflux condenser with a silica gel guard under an inert argon atmosphere. The mixture is stirred for 10 h at ambient temperature. It is hydrolyzed with a water-ice mixture (5 g) and then neutralized with a saturated sodium hydrogencarbonate solution to a pH of 6. The mixture is extracted with diethyl ether. The organic phase is dried and evaporated and the residue is recrystallized from pentane (the brown oils are purified by chromatography). White crystals are obtained (m=2.9 g, Yd=70%).

2) Procedure with Sulfuric Acid

Synthesis of 4-chlorophenyl trifluoromethyl sulfoxide

Sodium triflinate (2.11 g, 13.5 mmol), then 14 equivalents of sulfuric acid (18.3 g, 187 mmol), after stirring for a few minutes, one equivalent of monochlorobenzene (1.52 g, 13.5 mmol) are introduced into a three-necked flask surmounted by a reflux condenser with a silica gel guard under an argon atmosphere. The mixture is stirred for 21 h at ambient temperature. The medium is hydrolyzed with a water-ice mixture (5 g) and then with a saturated sodium hydrogen carbonate solution to pH 6, extraction is carried out with dichloromethane, and the organic phase is dried and then evaporated. A brown oil is obtained with a low yield of 15%.

Other aromatic compounds and the performances of the sulfinylation reactions in triflic acid or sulfuric acid are combined in the following table:

| Substrates | Products | Characterization of the products[a] | Experimental results |
|---|---|---|---|
| 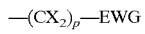 |  | $\delta(H_1) = 8.86$ ppm d<br>$\delta(H_2) = 8.73$ ppm t<br>$\delta(H_3) = 8.60$ ppm m<br>$\delta(CF_3) = -75.1$ ppm | Chemical Yd<br>ds $H_2SO_4$:<br>RY = 23.5%<br>DC = 24%<br>brown oil<br>ds $CF_3SO_3H$<br>polymerization |
| 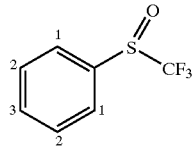 | 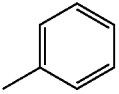 | $\delta(H_1) = 7.65$ ppm d<br>$\delta(H_2) = 7.37$ ppm d<br>$\delta(CH_3) = 2.42$ ppm s<br>$\delta(CF_3) = -72.5$ ppm | Yd:<br>ds $CF_3SO_3H$<br>RY 42%<br>DC 57%<br>ds $H_2SO_4$ crude isolated 50%<br>brown oil<br>* ortho/para: 25/75 |
| 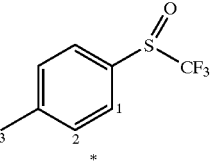 | 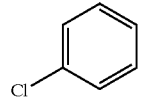 | $\delta(H_1) = 7.68$ ppm d<br>$\delta(H_2) = 7.52$ ppm d<br>$\delta(CF_3) = -75.5$ ppm | Crude isolated Yd:<br>ds $CF_3SO_3H$ 55%<br>ds $H_2SO_4$ 15%<br>brown oil<br>* ortho/para: 3/97 |

-continued

| Substrates | Products | Characterization of the products[a] | Experimental results |
|---|---|---|---|
| fluorobenzene | 4-fluorophenyl trifluoromethyl sulfoxide | $\delta (H_1) = 7.81$ ppm d*d<br>$\delta (H_2) = 7.31$ ppm d*d<br>$\delta (CF_3) = -75.4$ ppm<br>$\delta (F) = -104.4$ ppm | Crude Yd<br>ds $CF_3SO_3H$ 65%<br>brown oil<br>* ortho/para:<br>4/96 |
| 1,3-difluorobenzene | 2,4-difluorophenyl trifluoromethyl sulfoxide | $\delta (H_1) = 7.88$ ppm d*d<br>$\delta (H_2) = 6.9$ ppm t<br>$\delta (H_3) = 7.1$ ppm t<br>$\delta (CF_3) = -75.9$ ppm<br>$\delta (2\text{-}F) = -109.9$ ppm<br>$\delta (4\text{-}F) = -101.2$ ppm | Crude Yd<br>ds $CF_3SO_3H$ 70%<br>brown oil |
| 1,3-dichlorobenzene | 2,4-dichlorophenyl trifluoromethyl sulfoxide | $\delta (H_1) = 8$ ppm d<br>$\delta (H_2) = 7.6$ ppm d*d<br>$\delta (H_3) = 7.54$ ppm d<br>$\delta (CF_3) = -74$ ppm | Crude Yd<br>ds $CF_3SO_3H$ 70%<br>white crystals<br>M.p. = 61° C. |
| 1,3-dibromotoluene | 2,4-dibromo-6-methylphenyl trifluoromethyl sulfoxide | $\delta (H_1) = 7.67$ ppm d<br>$\delta (H_2) = 7.43$ ppm d<br>$\delta (CH_3) = 2.69$ ppm s<br>$\delta (CF_3) = -69.9$ ppm | Crude isolated<br>Yd > 70%<br>brown oil<br>* ortho/para:<br>17/83 |
| acetanilide | 4-(trifluoromethylsulfinyl)acetanilide | $\delta (H_1) = 7.81$ ppm d<br>$\delta (H_2) = 7.72$ ppm d<br>$\delta (CH_3) = 2.22$ ppm s<br>$\delta (CF_3) = -76.1$ ppm | Crude Yd<br>ds $CF_3SO_3H$ 40%<br>brown oil |
|  | 4-(trifluoromethylsulfinyl)aniline | $\delta (H_1) = 7.5$ ppm d<br>$\delta (H_2) = 6.8$ ppm d<br>$\delta (CF_3) = -76.8$ ppm | aniline/<br>acetanilide:<br>30/70 |
| trifluoromethoxybenzene | 4-(trifluoromethoxy)phenyl trifluoromethyl sulfoxide | $\delta (H_1) = 7.98$ ppm d<br>$\delta (H_2) = 7.62$ ppm d<br>$\delta (CF_3) = -70$ ppm<br>$\delta (OCF_3) = -58.2$ ppm | Crude Yd<br>ds $CF_3SO_3H$ 70%<br>DC > 90%<br>RY > 80%<br>brown oil<br>(appearance of crystals) |
| trifluoromethylbenzene | 3,5-bis(trifluoromethyl)phenyl trifluoromethyl sulfoxide | $\delta (H) = 7.8$ ppm m<br>$\delta (CF_3) = -64$ ppm<br>(sulfoxide)<br>$\delta (CF_3) = -43$ ppm | Crude Yd<br>ds $CF_3SO_3H$:<br>5 to 10%<br>impure product<br>brown oil |
| trifluoromethylthiobenzene | 4-(trifluoromethylthio)phenyl trifluoromethyl sulfoxide | $\delta (CF_3) = -74.3$ ppm<br>(sulfoxide)<br>$\delta (CF_3) = -42.1$ ppm | Crude Yd<br>20% |

Formation of Tolyl Tridecafluorohexyl Sulfoxide

A mixture of 10 ml of trifluoromethanesulfonic acid, 0.01 mol of sodium tridecafluorohexanesulfinate and 0.01 mol of toluene is stirred at ambient temperature for 17 h and then the mixture is hydrolyzed with ice, extracted with dichloromethane and dried over magnesium sulfate. The solvents are subsequently evaporated under vacuum; the residue is then chromatographed on silica with chloroform as eluent. A mixture is then obtained which comprises, by NMR, the ortho and para isomers of tolyl tridecafluorohexyl sulfoxide (o/p 1/9).

3) Procedure with a Third Solvent

Synthesis of 4-methylphenyl trifluoromethyl sulfoxide and of ditolyltrifluoromethylsulfonium triflate One equivalent of sodium triflinate (5.04 g, 32 mmol), 2 equivalents of toluene (5.97 g, 64 mmol), 5 equivalents of dichloromethane (13.6 g, 160 mmol) and then 1 equivalent of triflic anhydride (9.31 g, 33 mmol) are introduced into a three-necked round-bottomed flask surmounted by a silica gel guard under argon. The mixture is stirred at ambient temperature for 40 h, neutralized with a saturated sodium hydrogen carbonate solution and extracted with dichloromethane. The organic phase is dried and then evaporated. The crude yield of sulfoxide is of the order of 10% and of sulfonium of 60%. This brown oil is purified by chromatography with an ethyl acetate/pentane (1/30) mixture. Only the sulfoxide is eluted. The yield of 7% obtained after purification of the reaction corresponds only to the sulfoxide.

The following procedures describe, by way of indication, conversions of trifluoromethylated sulfoxides to trifluoromethylated sulfoniums:

4) Synthesis of (2,4-dichlorophenyl) phenyltrifluoromethylsulfonium triflate 2,4-Dichlorophenyl trifluoromethyl sulfoxide (0.71 g, 2.7 mmol), 20 ml of Fréon 113 (stored over $P_2O_5$), predistilled benzene (0.57 g, 7.3 mmol) and then triflic anhydride (1.48 g, 5.2 mmol) are introduced into a Schlenck tube placed under an inert atmosphere. The mixture is stirred for 4 days at ambient temperature (22° C.). The purification was not yet appropriate (chromatography on silica with the pentane/ ethyl acetate 30/1 mixture as eluent) and did not allow the pure product to be isolated. However, the product is obtained with a crude yield of 74%.

5) Synthesis of Diphenyltrifluoromethylsulfonium Triflate

Phenyl trifluoromethyl sulfoxide (0.4 g, 2.1 mmol) and then benzene (4.9 g, 64 mmol) are introduced, under an inert atmosphere and at approximately 0° C. (lower limit below which benzene crystallizes), into a Schlenck tube purged beforehand with argon. Five equivalents of triflic anhydride (2.82 g, 10 mmol) are gradually added. The mixture is stirred for 1 h at 0° C. and then for 24 h at ambient temperature. The medium is evaporated and the residue is purified by chromatography with the $CH_3CN/CH_2Cl_2$ (1/4) mixture as eluent. White crystals, having a melting point of 69–70° C., are obtained with a yield of 40%.

What is claimed is:

1. A process for the condensation of an aromatic compound and of a sulfinic compound, the carbonaceous chain of which is attached to the sulfinic functional group via a perhalogenated carbon atom, comprising the steps of:

a) carrying out a condensation reaction in a reaction mixture comprising said sulfinic compound, said aromatic compound and a strong acid which is an hydrohalic acid, a sulfonic acid, a perhalosulfonic acid, a flurosulfinic acid and sulfuric acid, and b) recovering the product obtained in step a).

2. A process according to claim 1, wherein said perhalogenated carbon atom is a perfluorinated carbon atom.

3. A process according to claim 1, wherein the reaction mixture has a water content maintained at a value such that the reaction mixture presents a $H_2O$/sulfinic functional group molar ratio of at most equal to 1.5.

4. A process according to claim 3, wherein the $H_2O$/ sulfinic functional group molar ratio is of at most 1.

5. A process according to claim 3, wherein the $H_2O$/strong acid functional group molar ratio is at most equal to 0.5.

6. A process according to claim 1, wherein the condensation reaction of step a) is carried out in the further presence of a dehydrating agent.

7. A process according to claim 1, wherein the condensation reaction of step a) is carried out in the further presence of an organic solvent.

8. A process according to claim 1, wherein the condensation reaction of step a) is carried out at a temperature at least equal to 0° C.

9. A process according to claim 8, wherein the reaction is carried out at a temperature at most equal to 50° C.

10. A process according to claim 1, wherein said carbonaceous chain is a perfluoroalkyl (Rf) group of formula:

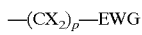

$—(CX_2)_p—EWG$ wherein:

the X groups, which are alike or different, represent a halogen or a radical of formula: $C_nF_{2n+1}$ with n being an integer of at most equal to 5 and wherein p represents an integer at most equal to 2; and EWG represents an electron-withdrawing group.

11. A process according to claim 10, wherein n is an integer at most equal to 8;

and Rf presents a total carbon number of between 1 and 15.

* * * * *